United States Patent [19]

Greco

[11] Patent Number: 5,084,201

[45] Date of Patent: Jan. 28, 1992

[54] SOLUBLE COPPER AMINO ALKOXIDES

[75] Inventor: Carl C. Greco, Garnerville, N.Y.

[73] Assignee: Akzo N.V., Arnheim, Netherlands

[21] Appl. No.: 480,705

[22] Filed: Feb. 15, 1990

Related U.S. Application Data

[63] Continuation-in-part of Ser. No. 270,570, Nov. 14, 1989, abandoned.

[51] Int. Cl.$^5$ .......................... C09K 3/00; C07F 1/08
[52] U.S. Cl. .................... 252/182.12; 505/1; 505/734; 505/802; 505/811; 556/1; 556/81; 556/113; 564/507
[58] Field of Search ............ 252/182.12; 556/113, 556/81, 1; 564/507; 505/1, 734, 802, 84

[56] References Cited

U.S. PATENT DOCUMENTS

| | | | |
|---|---|---|---|
| 2,147,226 | 2/1939 | Alquist et al. | 564/507 |
| 2,459,896 | 1/1949 | Schwarz | 556/113 |
| 2,850,497 | 9/1958 | Ehrhart et al. | 564/507 |
| 2,985,607 | 5/1961 | Koehler et al. | 556/81 |
| 2,989,412 | 6/1961 | Koehler et al. | 556/81 |
| 3,403,163 | 9/1968 | Fuchsman | 556/113 |
| 3,856,835 | 12/1974 | Guillot | 260/429.9 |
| 3,932,545 | 1/1976 | Screttas | 502/155 |
| 4,446,119 | 5/1984 | DuPart et al. | 252/189 |
| 4,847,239 | 7/1989 | Piotrowski et al. | 556/113 |
| 4,982,019 | 1/1991 | Purdy et al. | 505/734 |
| 5,001,110 | 3/1991 | Nonaka et al. | 505/734 |

FOREIGN PATENT DOCUMENTS

| | | | |
|---|---|---|---|
| 62-240691 | 10/1987 | Japan | 556/113 |
| 911762 | 11/1962 | United Kingdom | 556/113 |

OTHER PUBLICATIONS

Horowitz et al, *Science*, 243, 66-69 (Jan. 1989).

Primary Examiner—Edward A. Miller
Attorney, Agent, or Firm—Richard P. Fennelly; Louis A. Morris

[57] ABSTRACT

More storage stable solutions comprising an organic solvent containing a soluble copper amino alkoxide are disclosed. The compound is of the formula

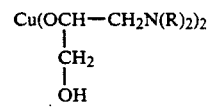

where and R is lower alkyl such as methyl or ethyl.

3 Claims, No Drawings

SOLUBLE COPPER AMINO ALKOXIDES

This is a continuation-in-part of U.S. Ser. No. 270,570, filed Nov. 14, 1988, now abandoned..

BACKGROUND OF THE INVENTION

Certain disclosures exist in the prior art in regard to copper amino alkoxide compositions, for example. For example, Japanese Patent Publication No. 62/240,691, dated Oct. 21, 1987, describes compounds of the general formula $Cu(ORNR'_2)_2$ where R is alkylene and at least one R' is hydroxyalkyl.

More recently, in Science (Jan. 6, 1989), Vol. 243, pp. 66-69 a hydrolyzable compound of the formula $Cu(OCH_2CH_2N(C_2H_5)_2)_2$, for example, is disclosed in regard to the formation of the superconductor $YBa_2Cu_3O_{6+x}$.

Related U.S. Ser. No. 270,570, filed Nov. 18, 1988, of Carl C. Greco et al. discloses certain metal (dialkylaminoalcoholate) solutions of the general formula $M(ORNR'_2)_2$, where M is a superconductor metal precursor (e.g., copper), R is alkylene of from 2 to 3 carbon atoms, and R' is alkyl of from 1 to 8 carbon atoms. Examples of suitable compounds which are given in this related application have the general formula $Cu(OCH_2CH_2NR'_2)_2$ where R' can be methyl or ethyl. Solutions containing such copper compounds, for example, dissolved therein can be formed but, upon standing for several weeks or more, some degree of undesired precipitation of the copper (dialkylaminoalcoholate) values originally dissolved therein.

U.S. Pat. No. 3,856,835 to D. G. Guillot describes various reaction products of an organometallic compound and an aminopolyol which are useful as catalyst compositions for the polymerization of an epoxide compound. Examples 11-12 describe the polymerization of propylene oxide in the presence of a catalyst formed by the reaction of diphenylmagnesium with a lower molar amount of either 3-dimethylamino-1,2-propanediol or 3-diethylamino-1,2-propanediol This patent fails to describe the structure of its catalyst composition other than indicating that some carbon-magnesium bonds remain unreacted. All of the Examples use a magnesium-containing organometallic reactant and do not employ any with such metals as zinc, aluminum, calcium, cadmium, strontium, gallium, or barium The compositions formed using the process described in the Guillot patent would be mixtures and not substantially pure heavy metal amino alkoxides as described herein.

SUMMARY OF THE INVENTION

Superior solutions having greater storage stability (i.e. a lessened tendency for precipitation of the metal compounds contained dissolved therein) can be formed in accordance with the present invention. The present invention relates to compounds of the general formula

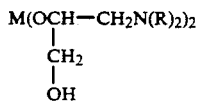

where M is a heavy metal (such as barium, lead, copper, or the like) and R is lower alkyl and to solutions containing them.

DETAILED DESCRIPTION OF THE INVENTION

The compounds of the present invention relate to heavy metal amino alkoxide compounds of the formula just given above where R can be lower alkyl of from about 1 to about 3 carbon atoms. Representative examples include those compounds where R is methyl or ethyl. The term "heavy metal" as used herein is deemed to be inclusive of those heavy metals having an atomic weight of about 60 or greater capable of forming the type of compounds depicted therein and are inclusive of such alkaline earth metals as barium and strontium and such transition metals as copper and lead. The metals are divalent and, when combined with the amino alkoxide ligands shown, are believed to be capable of six coordination sites The first two are believed to be covalent bonds with the oxygen atoms leading to the alkyl amino groups. The next two are believed to be coordination bonds between the electron rich hydroxy substituents. The last two are believed to be coordination bonds between the two electron rich nitrogen atoms of the amino functionality. However, this coordination explanation for the good solubility should be construed as no more than a possible theoretical explanation for the present invention by which the present applicant does not intend to be bound.

These compounds can be easily synthesized as described in greater detail in Examples 2 and 3 shown below by suspending the metal alkoxide, such as copper methoxide, in an appropriate organic solvent, such as tetrahydrofuran, followed by the addition of 3-(dialkylamino)-1,2-propanediol with appropriate heating of the mixture to bring about the appropriate exchange reaction and yield the solution containing the desired copper amino alkoxide therein. As demonstrated by a comparison of Example 4 and Comparative Example 5, below, the instant compounds have superior solubility over time as compared to the type of copper (dialkylaminoalcoholate) compounds covered in U.S. Ser. No. 270,570. Examples 6 and 7 illustrate synthesis of lead and barium amino alkoxides pursuant to this invention. The solutions have utility, for example, in forming superconductor precursor compositions which can be calcined to form a superconductor oxide composition.

The present invention, unlike the Guillot disclosure, allows for the production of the disclosed heavy metal amino alkoxides in substantially pure form substantially free of metal-carbon bonds since they are not synthesized using organometallic compounds as a reagent. The term "substantially pure" as used herein is intended to connote compositions of such heavy metal amino alkoxides which are free from the metal-carbon component which must be present in the Guillot compositions.

The present invention is further illustrated by the Examples which follow.

EXAMPLE 1

Copper (II) chloride (34 gm, 0.25 mole) was dissolved in 600 cc of methanol and 5 gm (0.725 mole) of lithium was then added. The solution was stirred for four hours at room temperature at the end of which a blue solid precipitate had formed. The precipitate was filtered from the reaction mixture and was washed four times with 250 cc of methanol each time The blue solid (copper methoxide) was vacuum dried and was used in Examples 2 and 3.

EXAMPLE 2

Copper methoxide (15 gm, 0.12 mole) from Example 1 was suspended in 350 cc of tetrahydrofuran at room temperature. To this was added, with good stirring, over a fifteen minute period, 35 gm of 3-(diethylamino)-1,2-propanediol (0.24 mole). The resulting solution was refluxed for one hour during which time 50 cc of solvent was removed. The solution was then collected as the product. Analysis showed 3.11% copper in solution. Therefore, according to the analysis, the amount of copper alkoxide of the formula

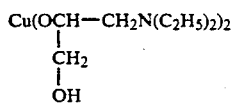

in solution was 17.4 gm or 9.2%, by weight.

EXAMPLE 3

Copper methoxide (10.5 gm, 0.084 mole) from Example 1 was suspended in 350 cc of toluene at room temperature. To this was added 24.6 gm of 3-(diethylamino)-1,2-propanediol (0.168 mole). The resulting solution was refluxed for two hours and was then stripped of solvent. Distillation was performed under slight vacuum using a pot temperature of around 80° C. A viscous oil remained as the product (29.8 gm). This oil was analyzed and was then redissolved in 211 gm of toluene to arrive at a concentration of the desired copper alkoxide, as in Example 2, of 12%, by weight The solution was stored in a dry box for about three months with no evidence of any precipitation.

EXAMPLE 4

In a 500 ml, one neck flask, was added 150 gm of the copper alkoxide-tetrahydrofuran solution from Example 2. This solution contained 3.11%, by weight, of copper (0.0735 mole). To this solution was added 190 gm of the barium alkoxide of diethylaminopropanediol in xylene solution. This solution contained 3.5%, by weight, barium (0.049 mole). Finally, there was added 59 gm of a solution of yttrium diethylaminoethoxide in xylene containing 3.7%, by weight, yttrium (0.0245 mole). The above solution was distilled at 80° C. under a vacuum of 80 mm of mercury to a final residue weight of 155 gm. The solutions therefore contained 3.02%, by weight, copper, 4.35%, by weight, barium, and 1.41%, by weight, yttrium. This solution was extremely storage stable with no signs of precipitation after standing two months.

COMPARATIVE EXAMPLE 5

In 600 cc of methanol was dissolved 34 gm of copper (II) chloride (0.253 mole) To this solution was added 5 gm of lithium (0.725 mole) The solution was stirred for four hours at room temperature At the end of this time there was formation of a blue solid precipitate (copper methoxide) The precipitate was filtered from the reaction mixture and was washed four times With 250 cc of methanol each time to remove LiCl and unreacted copper chloride. The blue solid was vacuum dried in the vacuum oven at 40° C. under nitrogen, and was then suspended in 400 cc of toluene. To this slurry was added 86 gm (0.76 mole) of diethylaminoethanol over a ten minute period. The reaction mixture was heated to 35° C. under a vacuum of 25 mm of mercury for forty-five minutes to remove the methanol. About 100 cc of methanol-toluene was distilled off during this time, keeping the pot temperature below 40° C. A clear dark blue solution resulted after the heating period and was diluted with more toluene to arrive at a final weight of 668 gm. The amount of copper alkoxide, of the formula $Cu(OCH_2CH_2N(Et)_2)_2$, in this solution was 74.8 gm or 11.2%, by weight.

The material was stored in a dry box for several weeks with no evidence of any precipitation A portion of this material was mixed with a solution of barium diethylaminoethoxide and allowed to stand at room temperature under nitrogen. This solution was also stable for many weeks. No sign of precipitation was noted. However, after one month's standing there was a slight formation of a precipitate in the original copper alkoxide solution. The amount of precipitation can be increased by heating the solution above 50° C. for only a few hours.

EXAMPLE 6

A one liter, three neck flask was equipped with a condenser thermometer, stirrer, and addition funnel Lead (II) acetylacetonate (40.5 gm) and 600 cc of xylene was added to the flask. To this slurry was then added 29.4 gm (0.2 mole) of 3-(diethylamino)1,2-propanediol under a blanket of nitrogen. The reaction was heated to reflux at which point all solids became soluble The reaction mixture was refluxed for two hours during which time 150 cc of solvent was distilled off. The distillation was required to remove by-product acetylacetone. The reaction mixture was filtered to remove a small amount of fines. The filtrate weight 328 gm and contained 6.3% lead. The yield was quantitative for lead diethylamino-hydroxypropoxide of the following formula:

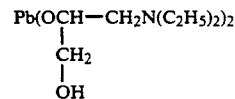

This lead compound can be spun coated onto an appropriate substrate and pyrolyzed to form a lead oxide coating.

EXAMPLE 7

To the same equipment used in Example 6 was added 16.4 gm (0.12 mole) of barium metal and 250 cc of xylene To the resulting slurry was added 35 gm (0.24 mole) of 3-(diethylamino)1,2-propanediol under a blanket of nitrogen. The reaction was heated to reflux and all solids solubilized as hydrogen was observed coming off from the reaction media. The reaction media was refluxed for two hours during which time most of the hydrogen was evolved. The reaction mixture was then filtered to remove a small amount of fines. The filtrate weighed 396 gm and contained 3.54% barium. The yield (83.3%) of the theoretical amount of the desired barium compound of the formula:

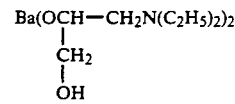

The amino alkoxides shown herein can be applied in organic coatings to an appropriate substrate and be pyrolyzed to form metal oxide films.

The foregoing Examples are provided to illustrate certain embodiments of the invention and should, for that reason, not be construed in a limiting sense. The scope of protection that is desired is set forth in the claims which follow.

I claim:

1. A substantially pure copper amino alkoxide of the formula

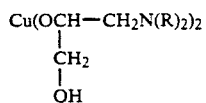

where R is lower alkyl.

2. Solutions comprising an organic solvent containing a copper amino alkoxide of the formula of claim 1 dissolved therein.

3. A process for forming the copper amino alkoxide of claim 1 which comprises reacting a copper alkoxide with a 3-(dialkylamino)-1,2-propanediol in solution.

* * * * *